(12) United States Patent
Slotkin et al.

(10) Patent No.: US 12,390,547 B2
(45) Date of Patent: *Aug. 19, 2025

(54) AGRICULTURAL PROACTIVE AIR/SURFACE DECONTAMINATION SYSTEM AND DEVICES

(71) Applicant: Radical Clean Solutions Ltd., Long Beach, NY (US)

(72) Inventors: Roger Slotkin, Long Beach, NY (US); Ralph T. Kubitzki, Plantation, FL (US)

(73) Assignee: Radical clean Solutions, Ltd., Long Beach, NY (US)

(*) Notice: Subject to any disclaimer, the term of this patent is extended or adjusted under 35 U.S.C. 154(b) by 304 days.

This patent is subject to a terminal disclaimer.

(21) Appl. No.: 17/674,763

(22) Filed: Feb. 17, 2022

(65) Prior Publication Data
US 2023/0173125 A1 Jun. 8, 2023

Related U.S. Application Data

(63) Continuation-in-part of application No. 17/545,919, filed on Dec. 8, 2021.

(51) Int. Cl.
*A01G 31/02* (2006.01)
*A61L 2/26* (2006.01)
(Continued)

(52) U.S. Cl.
CPC .............. *A61L 9/04* (2013.01); *A01G 31/02* (2013.01); *A61L 2/26* (2013.01); *A61L 9/20* (2013.01);
(Continued)

(58) Field of Classification Search
CPC ........ A01G 31/02; A01G 31/06; A01G 9/246; A01G 9/249; A01G 27/00; A01G 31/023;
(Continued)

(56) References Cited

U.S. PATENT DOCUMENTS 2,945,554 A 7/1960 Berly
3,949,522 A 4/1976 Kehl et al.
(Continued)

FOREIGN PATENT DOCUMENTS

JP 2010080195 A 4/2010
KR 2021073421 A * 6/2021 .............. A01G 9/24
(Continued)

OTHER PUBLICATIONS

LSE (Light Spectrum Enterprises); "Shop UV Lighting-GPH457T5L/4P Ultraviolet UV Lamp Bulb 4-pin Base 18" GPH457T5; 1300 Industrial Blvd.-Ste B3, Southampton, PA 18966.
(Continued)

*Primary Examiner* — Monica L Perry
(74) *Attorney, Agent, or Firm* — Alfred M. Walker (57) ABSTRACT

A system for decontaminating/neutralizing breathable air and surfaces in an occupied enclosed space, i.e., agricultural greenhouse, includes mounting an atmospheric hydroxyl radical generator along an inside surface of the atmospheric hydroxyl radical generator having respective opposite air inlets and air outlets. The hydroxyl radical generator includes a polygonal housing supporting a plurality of spaced crystal-spliced UV optics, which are tubular, medical grade pure quartz optics to emit/irradiate ultraviolet in the nanometer wavelength/ultraviolet spectrum of between 100 and 400 nanometers for deactivating and neutralizing atmospheric chemicals and pathogens in breathable air and surfaces. The hydroxyl radicals contact the walls of the reaction chamber housing. The hydroxyl radicals become created and excited to react quickly with impurities including VOC, virus, bacteria and fungi, rendering them inactivated and neutral. The breathable air passes through the polygonal housing and is decontaminated and neutralized of impurities before entering the occupied enclosed space.

23 Claims, 7 Drawing Sheets

(51) Int. Cl.
*A61L 9/04* (2006.01)
*A61L 9/20* (2006.01)

(52) U.S. Cl.
CPC .......... *A01G 31/065* (2025.01); *A61L 2202/11* (2013.01); *A61L 2202/25* (2013.01); *A61L 2209/12* (2013.01); *A61L 2209/21* (2013.01)

(58) Field of Classification Search
CPC .............. A01G 31/0232; A01G 31/065; A01G 31/011; A01G 7/06; Y02A 40/25; A61L 2202/11; A61L 2202/25; A61L 2209/12; A61L 9/20; A61L 2/10; A61L 9/22
See application file for complete search history.

(56) References Cited

U.S. PATENT DOCUMENTS

| | | |
|---|---|---|
| 6,497,840 B1 | 12/2002 | Palestro et al. |
| 6,613,277 B1 | 9/2003 | Monagan |
| 6,805,733 B2 | 10/2004 | Engel et al. |
| 6,967,008 B1* | 11/2005 | Barnes .................. A01M 29/12 422/186.07 |
| 7,837,933 B2 | 11/2010 | Sevack et al. |
| 7,976,195 B2 | 7/2011 | Engel et al. |
| 7,988,923 B2 | 8/2011 | Fink et al. |
| 8,252,099 B2 | 8/2012 | Worrilow |
| 8,252,100 B2 | 8/2012 | Worrilow |
| 8,545,753 B2 | 10/2013 | Sevack et al. |
| 8,747,753 B2 | 6/2014 | Engel et al. |
| 9,168,323 B2 | 10/2015 | Morneault |
| 9,522,210 B2 | 12/2016 | Worrilow |
| 9,675,725 B2 | 6/2017 | Worrilow |
| 9,884,135 B2 | 2/2018 | Bystrzynski et al. |
| 9,937,466 B2* | 4/2018 | Mitch .................. B01D 53/007 |
| 9,956,306 B2 | 5/2018 | Brais et al. |
| 9,980,748 B2 | 5/2018 | Worrilow |
| 10,857,249 B2 | 12/2020 | Brais et al. |
| 11,103,611 B2 | 8/2021 | Elde et al. |
| 2003/0230477 A1* | 12/2003 | Fink .......................... C01B 13/10 204/157.44 |
| 2004/0052680 A1* | 3/2004 | Elwood ..................... A61L 9/20 422/24 |
| 2008/0073565 A1 | 3/2008 | Jeon |
| 2009/0020016 A1* | 1/2009 | Christophersen ......... A61L 9/20 96/224 |
| 2010/0244253 A1* | 9/2010 | Yeom ................ H01L 21/76861 438/653 |
| 2014/0314627 A1* | 10/2014 | Morneault ................ A61L 9/20 422/121 |
| 2015/0114822 A1 | 4/2015 | Greco |
| 2016/0102025 A1* | 4/2016 | Nunnally ................. A01G 7/06 422/162 |
| 2017/0225973 A1 | 8/2017 | Henderson et al. |
| 2019/0045731 A1* | 2/2019 | Dixon .................... A01G 31/02 |
| 2019/0289803 A1* | 9/2019 | Gagne ..................... A01G 9/246 |
| 2020/0029972 A1 | 1/2020 | Jordan et al. |
| 2020/0084983 A1 | 3/2020 | Liang et al. |

FOREIGN PATENT DOCUMENTS

| | | | |
|---|---|---|---|
| WO | WO-2008088108 A1 * | 7/2008 | ............. A01G 9/023 |
| WO | WO2020176993 A1 | 9/2020 | |
| WO | PCT/US2022/051886 A | 5/2023 | |

OTHER PUBLICATIONS

Hao Chen, et al.; "A Hydroxyl radical detection system using gas expansion and fast gating laser-induced fluorescence techniques"; The Research Center for Eco-Environmental Sciences, Chinese Academy of Sciences; Journal of Environmental Sciences 65 (2018) 190-200; published by Elsevier B.V.; http/dx.doi.org/10.1016/i.jes.2017.03.012.

AIRGROW; "Control Temperature, Ventilation and Humidity in the Grow Room"; Sales Brochure; PO Box 5206, Manchester, NH 03018.

GrowSaver™ by Sanuvox; "The Most Effective & Economical Way to Prevent Powdery Mildew"; download Jun. 24, 2022; https://growsaver.net/en/.

"Greenhouses/Heating, Cooling and Ventilation"; University of Georgia/Extension; Bulletin 792; reviewed Dec. 2014; extension.uga.edu.

Editor; "Canivate: Redefining the Standard for Cannabis Growth"; Canivate Growing Sytems Ltd.; last update Jul. 17, 2020; Business Television News; download Jun. 22, 2022.

\* cited by examiner

AGRICULTURAL PROACTIVE AIR/SURFACE DECONTAMINATION SYSTEM AND DEVICES

FIELD OF THE INVENTION

The present invention relates use of a harmonic biomimicry nonchemical photonic process that results in the export of desired atmospheric hydroxyls at precisely the same rate as nature provides (2.6 million per cubic Centimeter—NASA), to neutralize toxic chemicals and pathogens in breathable air/surfaces in stationary or moving human occupied spaces.

BACKGROUND OF THE INVENTION

Ultraviolet light (UV) delivery in the form of directing ultraviolet light on unsanitary surfaces as germicides, bactericides and viricides are disadvantageous because, upon exposure to seating fabrics in aircraft and land vehicles, the ultraviolet light—compromises fabrics and doesn't penetrate into crevices between, or in, passenger seats. Delivery of ultraviolet light for sanitation is limited because the ultraviolet light is only as effective as the actual line of sight of the ultraviolet waves.

DESCRIPTION OF THE PRIOR ART

Methods of Producing Atmospheric Hydroxyls

In the field of physics there are, to date, only a few processes in a device that generates an atmospheric hydroxyl that purportedly are useful in removing contaminants from breathable air. In theory the NASA device produces the hydroxyl in a photo catalytic oxidation (PCO) process, by emitting an ultraviolet irradiation of 254 nanometers as it interfaces with titanium dioxide ($TiO_2$) plating. In theory, the hydroxyl is produced only at the interface site of contact at the surface of the $TiO_2$. The hydroxyl does not exit the airstream and does not have any downstream interaction. Minimal air flow must be maintained at approximately 120 cfm. Typical HVAC systems utilize faster air movement at approximately 2000 cfm and this would not allow for the theoretical hydroxyl to form.

OBJECTS AND SUMMARY OF THE INVENTION

In contrast, the present invention uses airborne hydroxyl radical molecules, which are of very small molar size and can occupy almost any given space. They can occupy dark crevices that ultraviolet line of sight cannot get access to. The present invention allows for a "Harmonic" of photonic UV frequencies to be applied within a hydroxyl producing reaction chamber. The feed stock is ambient water vapor in air which will have relative humidity, this humidity is the feed stock for the reaction chamber to produce the atmospheric hydroxyl.

This action is called "Bio-Mimicry". The present invention process is a totally green, nonchemical process that results in the export of the desired atmospheric hydroxyl at precisely the same rate as nature provides, namely, at 2.6 million per cubic centimeter. The atmospheric hydroxyl process begins by exposing ambient water vapor to special UV optics having hydroxyl activation portions made of medical grade pure quartz material. The optics are designed to emit/irradiate Ultraviolet irradiation in the nanometer wavelength/Ultraviolet spectrum of between 100 and 400 nanometers, thereby producing the hydroxyls at the aforementioned quantity of 2.6 million hydroxyls per cubic centimeter, as provided in nature. This is a novel improvement over prior art NASA PCO based technology.

Hydroxyl are groups having the radical "—OH" and are represented by the symbol —OH or HO—, which can have a negative charge or be neutral. The hydroxyl functional group includes one hydrogen atom which is covalently bonded to one oxygen atom. Hydroxyl radicals are very reactive, which react quickly to hydrocarbons, carbon monoxide molecules and other air impurities, such as volatile organic compounds, (VOC), virus, bacteria and fungi.

Many closed HVAC air systems can harbor microscopic bacteria, virus (i.e., Covid-19) and fungi.

Therefore, the present invention is a unique and novel application method of for the delivery of safe and natural hydroxyl radicals into breathable air volume containers such as agricultural hydroponic greenhouses and the agricultural plant contents therein. To be considered as well are upholstered chair seats, benches, contact surfaces such as grab bars, handles, etc.

In the present invention, the atmospheric hydroxyl radicals are generated in closed multi-sided housing, preferably polygonal, having therein two or more parallel UV optics which are multi segmented with crystal, so that when enabled, the hydroxyl radicals are generated. Hydroxyls are reactive and short lived, however the closed housing reaction chamber preferably has polygonal interior walls, so that the hydroxyl radicals will bounce against the walls so as to decontaminate within the reaction chamber as well as downstream in open air areas. Breathable air is then directed through the closed housing, so that the created and excited radicals will react quickly to air and surface impurities, such as pathogens and VOC's, rendering them neutral.

The UV optics are tubular, medical grade pure quartz. The optics are designed to emit/irradiate Ultraviolet irradiation in the nanometer wavelength/Ultraviolet spectrum of between 100 and 400 nanometers.

A multi wave 'Harmonic' is created via a multiwavelength nanometer configured optic irradiation. This configuration results in the creation of the desired atmospheric hydroxyl within the hydroxyl generator reaction chamber, which is a multi-sided reaction chamber, designed in such a way as to optimize atmospheric downstream hydroxyl production, such as for example in a polygonal-shaped housing. This multi-sided reaction chamber enables the desired atmospheric hydroxyl to be injected downstream to affect positive change. The positive change is the control/neutralization of pathogens and VOC's.

The —OH formed hydroxyl molecule is the capacitor that donates electrons to the targeted pathogen, whereupon the pathogen is therefore neutralized by the 'Electron Voltage (eV')' capacitance carried by the hydroxyl. The eV is donated at the point of contact with the pathogen.

VOC's are neutralized through the action of Bond Dissociation Energy (BDE). The capacitance of the charged hydroxyl is sufficient so as to take out of phase (decomposition) of any airborne molecular or compound structure. In Phase VOC chemistry can be harmful; therefore out-of-phase atomic airborne structures are now neutral and cannot recombine. The exception to this rule would be the recombination of water vapor, carbon dioxide and lastly oxygen ($O_2$).

This reaction sequence is essential to all life, in that water vapor feeds all life, and carbon dioxide ($CO_2$) is necessary/essential for plant life and oxygen ($O_2$) is essential for air breathers such as human, other animals and forms of living organisms. Because exposure of the UV light is problematic for human eyes, the interior of the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

The agricultural hydroxyl generating units also have communications capabilities, so that the Hydroxyl Generating Device can interface with a remote-control pad or mobile phone.

Safety features include a microswitch which will shut off from inadvertent opening if the reaction chamber device is "on" when it should be "off". The micro switch shuts down all systems should the device be opened when the generating unit is in operational status.

Anti-Vibration G-Force Mitigation Clips are installed, such as spring clips which operate in only one directional installation.

Reactor Rod Safety is paramount, for prevention of Reactor Rod displacement and breakage.

The agricultural hydroponic hydroxyl generating unit also includes custom designed noise reduction adhesive pads, and strategically placed self-adhesive sound/vibration reduction material wall insulation to mitigate sound and vibration. Building HVAC units in general have the above features, but where the optics are provided in a two optic array of a-b options, where "A" is on, but "B" is on if A fails.

No fan assembly is needed because the HVAC system has its own air movement capability. In a double optic option one optic may be on to create the hydroxyl radical and the existing HVAC fan directs the hydroxyls with the dual optic availability, should there be an abnormal intrusion of VOCs' or pathogens into the HVAC system, then the sensor would alert the hydroxyl device and the second optic would then come online in order to neutralize the threat load.

For safety, an air pressure safety switch is provided, so that when air flow is not detected, this unit will be dormant. A Micro Switch shuts down all systems should the device be opened when unit is in the ON/RUN position.

EXAMPLES

Greenhouse Hydroponic Installation

In hydroponic or other greenhouses, as in Nature, the atmospheric hydroxyls are lighter than air, so they are provided below plant growing media, such as of coconut fiber, vermiculite, etc., wherein the hydroxyls located from below flow up around the roots and growing media; being lighter than O2, the hydroxyls "drift upward". They will not penetrate fluid or solids, so parts of the roots and media must be exposed to hydroxylated air, as opposed to being in fluid or soil. This greenhouse installation also uses a 2×2 lamp array and has the same options as in the large building HVAC duct installation.

BRIEF DESCRIPTION OF THE DRAWINGS

The present invention can best be understood in connection with the following drawings, which are not deemed to be limiting in scope.

DETAILED DESCRIPTION OF THE DRAWINGS

Figures 1, 2:
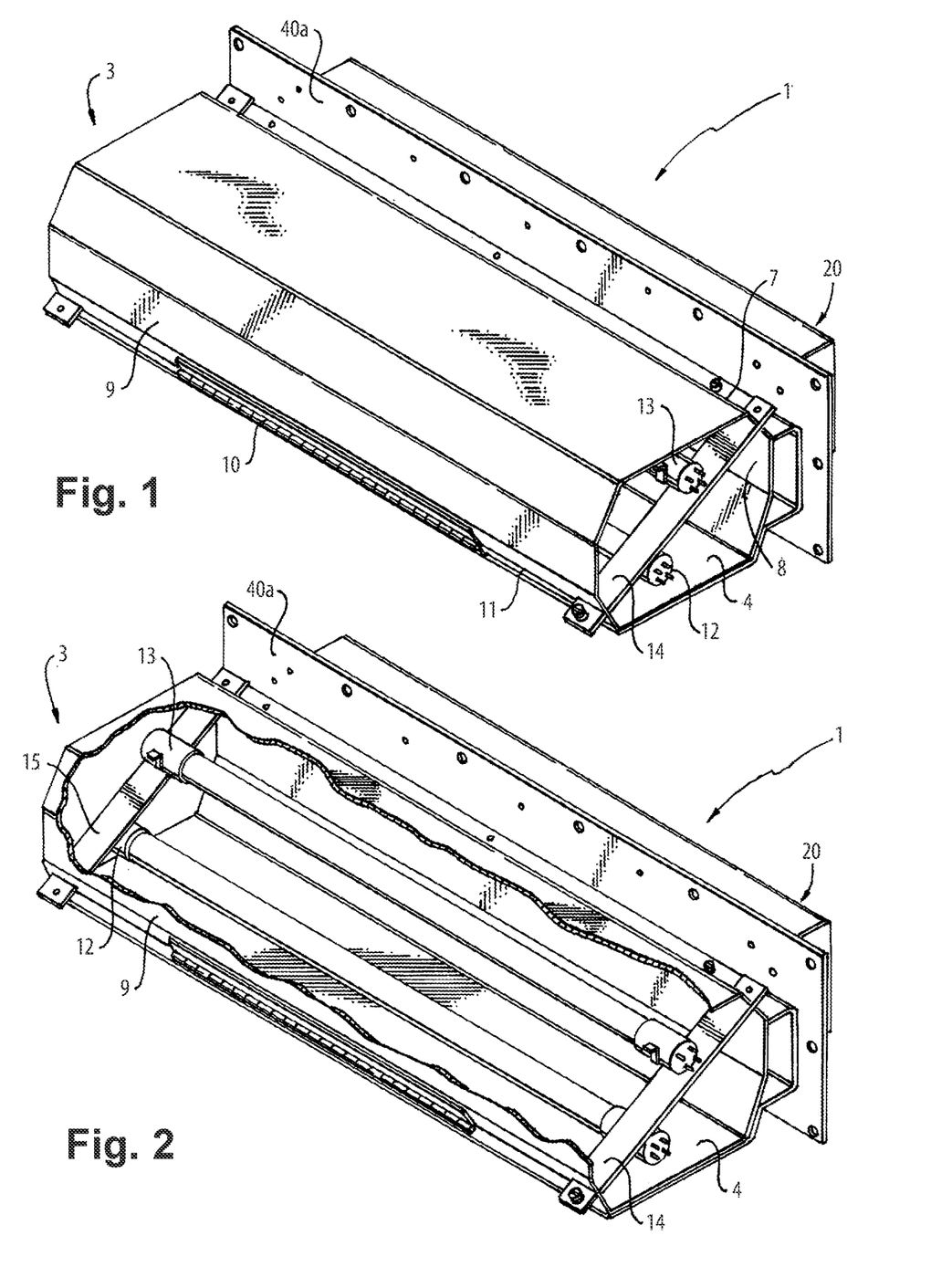
FIG. 1 is a perspective view of a polygonal hydroxyl generator shown in a closed position.
FIG. 2 is a perspective view of the hydroxyl generator of FIG. 1 shown in partial crossection with an open view of the interior of the hydroxyl generator.

FIG. 1 shows a hydroxyl generator 1, including a polygonal-shaped housing, including a bracket brace 14 for crystal-spliced UV optics 12 and 13, which are mounted parallel to each other inside the clamshell hexagon housing, but staggered so that UV optic 12 is on a different side of the bracket 14 from the side on which UV optic 13 is located, wherein the crystal spliced UV optics 12 and 13 each have a length that runs substantially the entire length of the housing of the hydroxyl generator 1. A preferred example for the crystal-spliced UV optics 12 and 13 is the GPH457T5L/4P UV Optic 4-pin Base 18" GPH457T5 of Light Spectrum Enterprises of Southampton these optics 12 and 13 are typically 18 inches long and are made of quartz. The tubular optics 12 and 13 are composed of pure Medical Grade quartz crystal in the portion of the optics which creates the hydroxyls. The present invention adds additional frequencies to the pure crystal optics. This tubular lamp optics 12 and 13 generate 'Harmonic' bio-mimicry nonchemical process of the present invention enables the production of desired atmospheric hydroxyls at a rate commensurate with the VOC/Bio loading in that particular space to be treated with the hydroxyls.

In contrast to the medical grade quartz tubular optics, it is noted that total glass tubes cannot be used when generating UV. The glass would simply be vaporized. Some companies use a fusion of glass and quartz crystal, which is not optimal as the glass portion creates a frequency that actually attracts contaminants. This problematic action neutralizes the desired UV action. Such a fusion lamp of glass and quartz crystal is cheaper to produce, however the poor performance of the lamp would be the end result.

Figure 3:
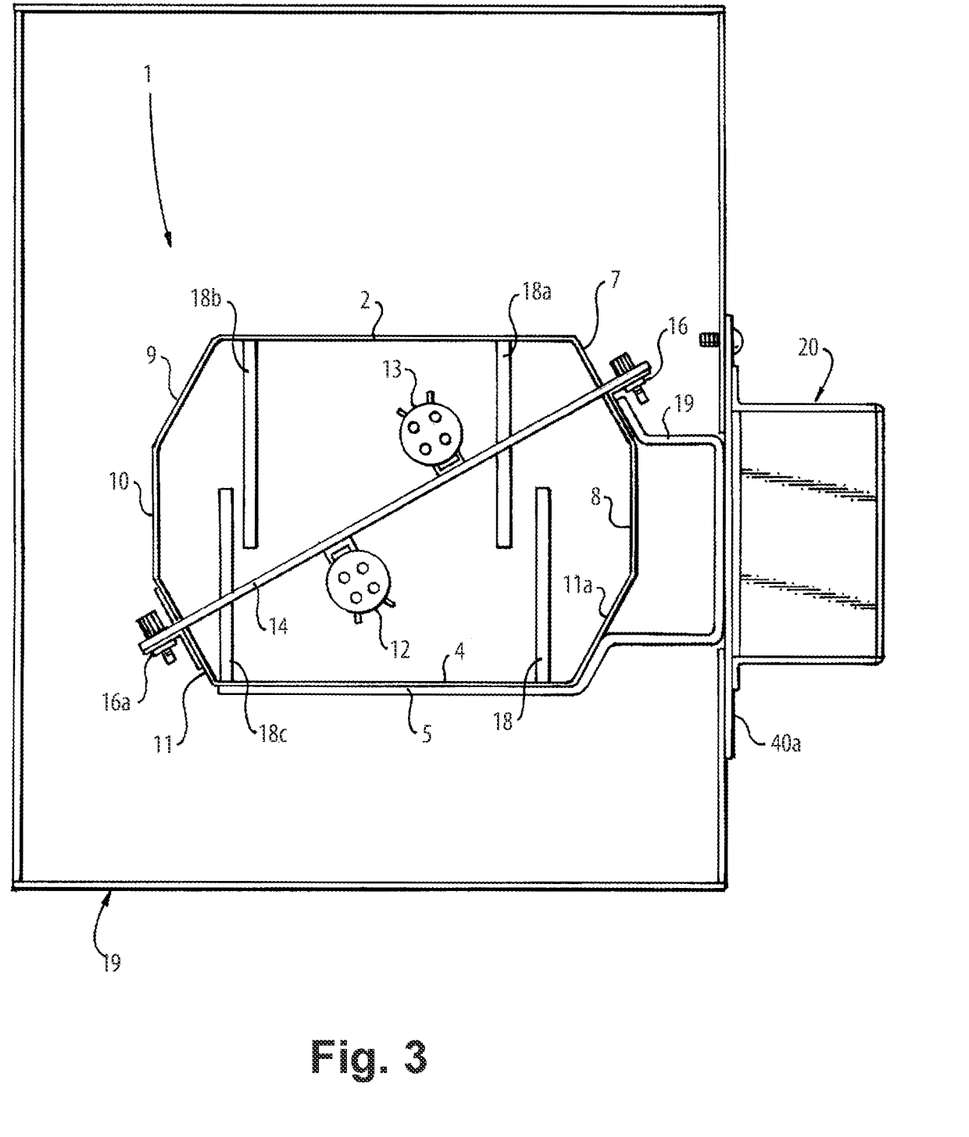
FIG. 3 is an end view in crossection of the hydroxyl generator of FIG. 1, with two UV optics for generating hydroxyl radicals.
Figure 4:
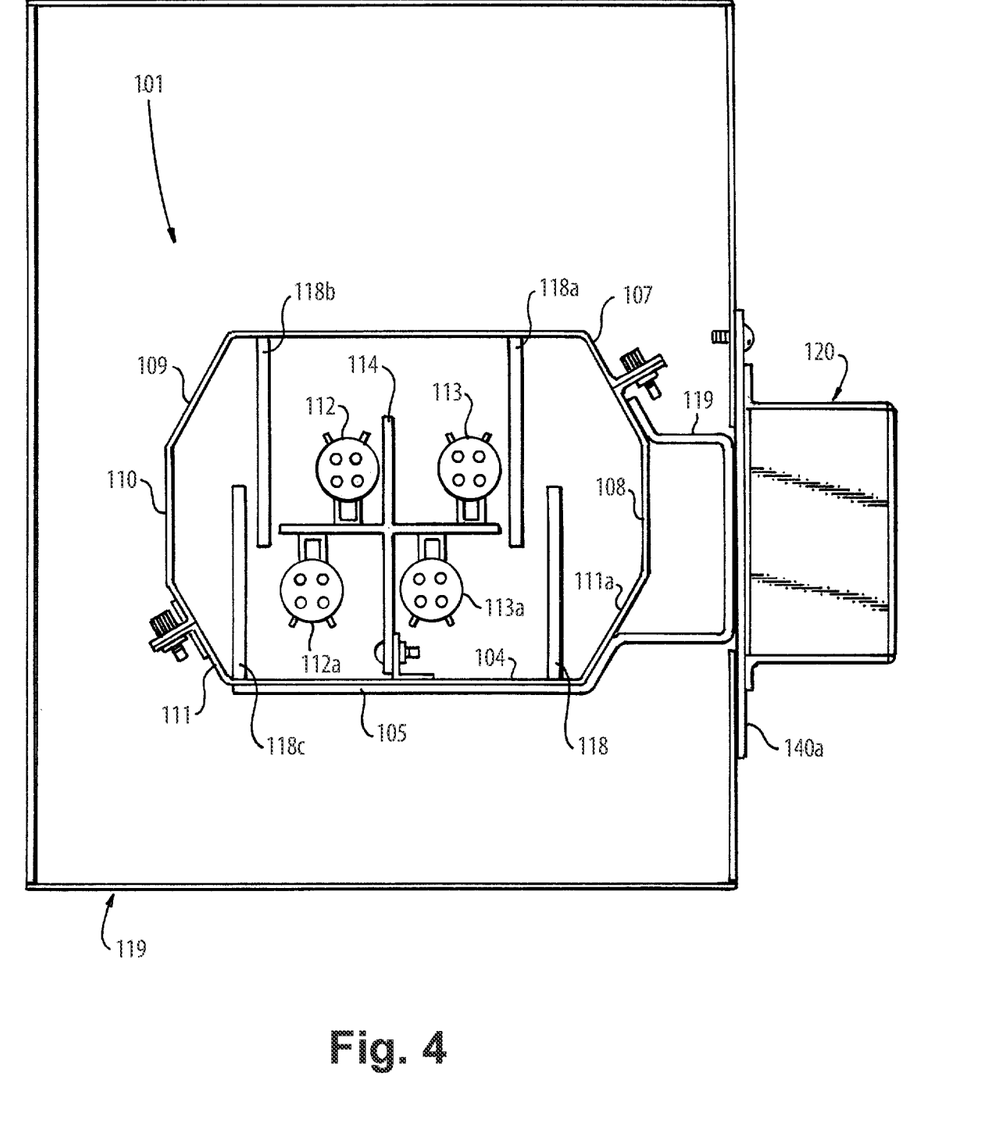
FIG. 4 is a crossectional end view of an alternate embodiment for a hydroxyl generator, showing four UV hydroxyl generator optics within the polygonal hydroxyl generator.

Other similar Medical Grade quartz tubed UV optics can be used. The optic 12 and 13 are preferably symmetrically positioned in the housing of the hydroxyl generator 1, as shown in FIGS. 3 and 4 to operate most efficiently, but where in FIG. 3 the crystal spliced UV optics 12 and 13 are staggered so that UV optic 12 is on a different side of the bracket brace 14 from the side on which UV optic 13 is located. FIG. 4 shows an alternate embodiment where there are two pairs of UV optics, namely 112, 113 and 112a, 113a. The UV optics 112, 113 are staggered to the right on one side of the horizontal bracket brace, but are separated by upright bracket brace 114. Likewise, UV optics 112a and 113a are staggered to the left on the opposite side of the horizontal bracket brace, also separated from each other by upright bracket brace 114.

The clamshell hexagon housing hydroxyl generator 1 has a clamshell configuration, including a clamshell top wall 2, upper side walls 7, 8, 9 and 10, a hinge 6 for opening the polygonal clamshell housing 1 and a bottom clamshell portion, including a bottom wall 4 and angle-oriented walls 11 and 11a, whereby the polygon housing opens hinge 6 to expose the inside of the hydroxyl generator 1 for maintenance and/or repair. In addition, the polygon hydroxyl generator enclosure can be removed from the air duct wall 40A for such maintenance and repair. The hydroxyl generator also includes an adjacent electronic control box 20, which is attachable to the clamshell housing of the hydroxyl generator 1. Alternatively, as shown in FIGS. 3 and 4, the electronic control box 20 is preferably located outside of the air path, which may be a duct or other conduit. it can alternatively be attached outside of the duct. It communicates with the UV optics wirelessly. The reason for the polygon shape is that the hydroxyl generators generated by the crystal-spliced UV optics 12 and 13 are scattered upon being generated by the optics 12 and 13, but they dissipate quickly if not activated by contact with reflective non-absorbent surfaces inside the respective walls of the polygon. The purpose of the polygon shape is that when the hydroxyl radicals are generated, they are emitted radially in all directions from the UV crystal-spliced optics 12 and 13 and normally would dissipate when scattered radially from the optics. In order to permit the hydroxyl radicals to maintain their desired electron charge and ability to contact and inactivate mold, volatile organic compounds, pathogens, bacteria, virus, etc., they need to reflect and refract off of the reflective non-absorbent walls continuously, within the reaction chamber confined space. As atmospheric hydroxyls are being activated by being created and excited in back-and-forth activity, the air inside the air duct/plenum 40a will contact the activated hydroxyl radicals with the end result of the neutralization of any impurities, such as VOCs, virus, bacteria, fungi, etc., in the air and surfaces.

Furthermore, once these radicals are emitted, they can penetrate any crevices in any area, such as between seats of mass transit vehicles, between the surfaces of desks; anywhere where ultraviolet light by itself would not be capable of eradicating the undesirable VOCs, fungi, virus, bacteria, etc. The polygon-shaped housing is strategically located within an air duct wall, which can be in a building which has sub walls extending to various rooms in the building.

As shown in the end view of FIG. 3, the inside of the polygon housing 1 is located below the field of vision within the sealed off plenum so that the ultraviolet (UV) crystal-spliced tubular optics 12 and 13 will not be exposed to the eyes of any observers. Therefore, while the hydroxyl radicals are being generated, the UV energy which create hydroxyl generation from optics 12 and 13 are completely sealed off so that when the optics 12 and 13 are operational, the UV light emanating therefrom will not penetrate outside of the polygonal housing. There is no restriction regarding the active flow of the hydroxyls inside the hydroxyl generator 1 and no interference with the excitement of the hydroxyls produced by the exposure of ambient water vapor within the polygon shaped housing with the UV optics 12 and 13 irradiating light that causes the —OH radicals to form.

FIG. 4 shows an alternate embodiment for a four optic version, where polygon hydroxyl generator enclosure 101, having top wall 102, side walls 107, 108, 109, 110 of an upper shell, as well as lower walls 105, 111a, 111b of the clamshell housing. FIG. 4 also shows the electronics control box 120.

Figure 5:
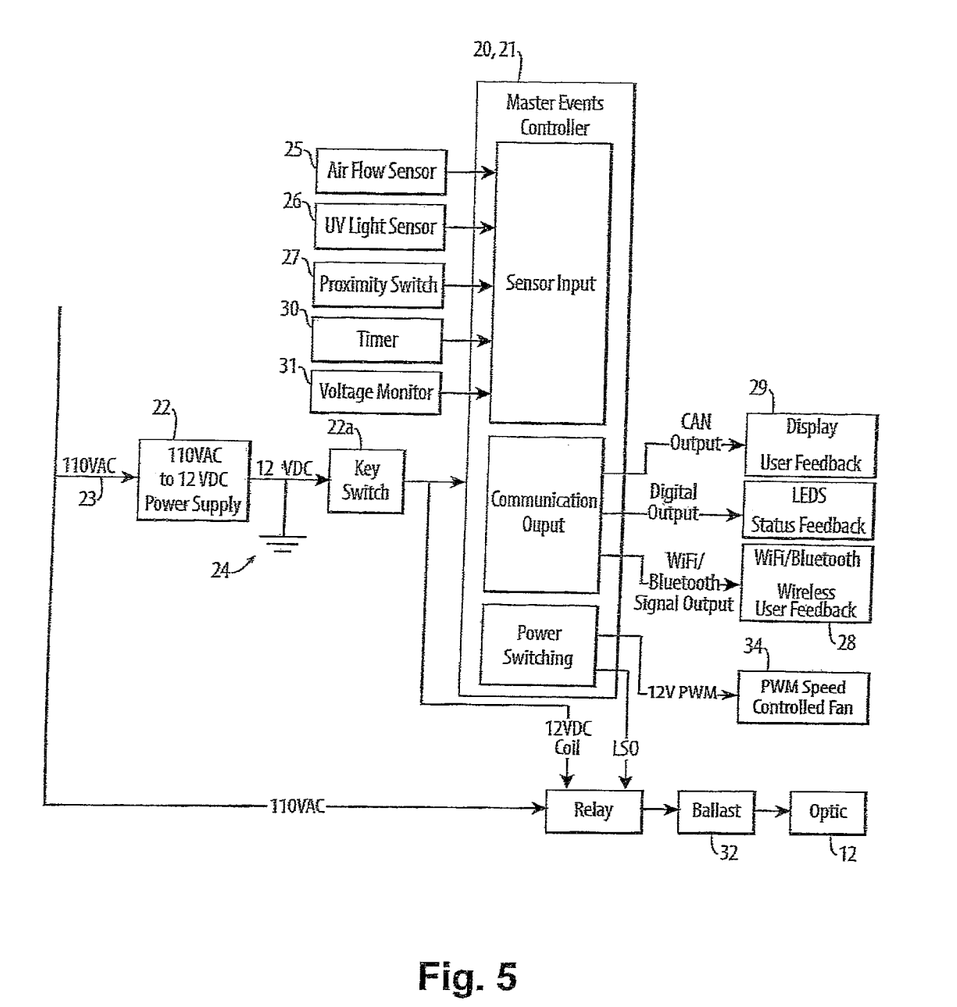
FIG. 5 is a block diagram of the electronic controls of the hydroxyl generator of FIGS. 1-3 and 4.

FIG. 5 is a block diagram showing the network and electronics of the control box 20. Initially AC power 23 of 110 VAC is converted by converter 22 to low voltage 12 VDC, or else a low voltage battery alternatively delivers 12 VDC to a secure Key Switch 22a, to provide power to the Master Events Controller 20, which may have a microprocessor 21. The Master Events Controller 20 also receives input from sensors, such as Air Flow Sensor 25, UV Light Sensor 26, Proximity Switch 27 (detecting opening of the enclosure), Timer 30 and Voltage Monitor Sensor 31. These sensors provide Sensor Input to the Master Events Controller 20. Power Switching in the Master Events Controller 20 sends 12V Pulse Width Modulation data to a PWM Speed Controlled Fan 34, to send air through the hydroxyl generator unit 1 or 101, or to stop the flow of air when needed for safety and maintenance situations. The Power Switching also sends data via a Large Serve Outlet (LSO) to a Relay, which controls the Ballast 32, providing power to the Crystal UV Optics 12, which creates the needed hydroxyls within the hydroxyl generators 1 or 101. The Master Events Controller 20 also has a Communications Output, which can send data via a Controller Area Network (CAN) to a Visual Display 29 for user feedback. The Communications Output of the Master Events Controller 20 also sends digital data wirelessly as output to Status Feedback Units. The Communications Output of the Master Events Controller 20 also sends Wi-Fi/Bluetooth Signal output to Wireless input devices 28 for Wireless user feedback during use.

Figure 5A:
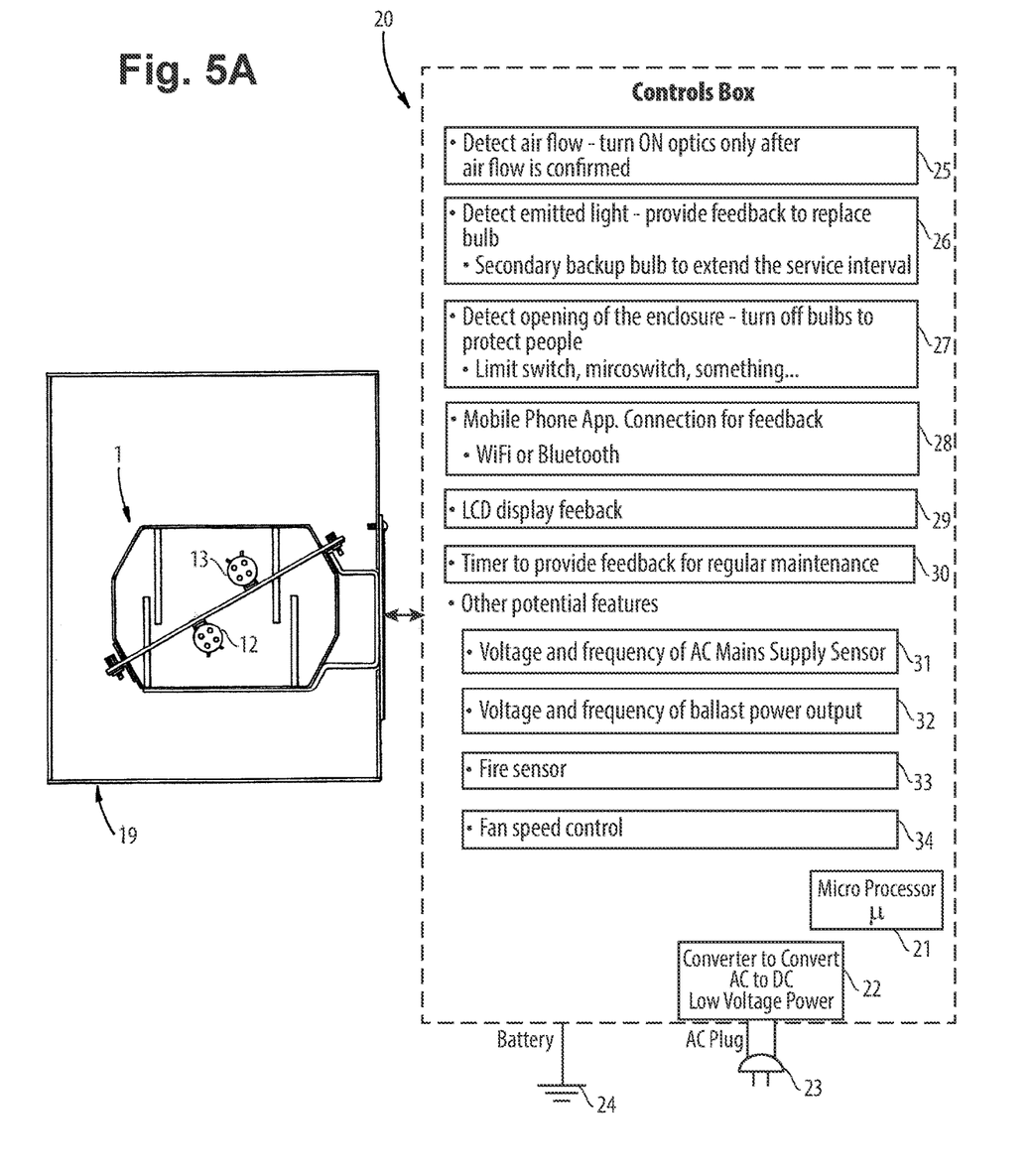
FIG. 5A is a flow chart showing the electronic controls with respect to their position adjacent to the hydroxyl generator.

FIG. 5A is a diagrammatic flow chart, showing the electronic control box 20 of FIGS. 1, 2 and 3, which is also equivalent to the electronic control box 120 of FIG. 4. Adjacent to the hydroxyl generator 1 or 101, which in FIGS. 1-3, the hydroxyl generators are attached by brackets 19 to the electronic control box 20. Similarly, the electronic control box 120 is attached by brackets 119 of FIG. 4.

In the diagrammatic flow chart of FIG. 5A, related to the electrical block diagram of FIG. 5, the control box 20 includes a microprocessor 21 for controlling the sensors and switches, which control the operation of the optics 12 and 13, or 112 and 113, of FIGS. 1-3 and 4. There is also a power source being either a DC low-voltage battery 24, or an AC plug 23, to provide higher-voltage AC power. When the AC is used, a converter 22 can be provided to convert high-voltage AC to low-voltage DC power for operating any of the sensors and control elements within box 20. The controls include a detector 25 to detect whether airflow is on, so that the optics 12 and 13 will only be on after airflow is confirmed, so that they are not on when there is no airflow. In the sensor for detecting emitted light, and providing feedback to replace optics, including a secondary backup optic, is provided at box 26 of the flowchart. Box 27 is a detector for opening of the enclosure, to turn off the optics to protect people from being exposed to the possible harmful UV light emitted from the optics 12 and 13. This detection also includes a limit switch, a micro switch and sensors. Box 28 is a mobile phone application for connection for feedback by wireless communication, such as Wi-Fi or Bluetooth® communications between the operator and the control box and hydroxyl generator itself. The control box also includes an LCD display feedback system 29, as well as a timer 30 to provide feedback for regular maintenance. Voltage and frequency of AC main supply sensor 31 is provided and voltage and frequency of the monitor of the ballast and power outfit 32 is also provided. A fire sensor 33 detects excess heat in the system and a fan speed control 34 controls any fans for providing and activating the airflow through the polygon hydroxyl generators.

Figures 6, 6A:
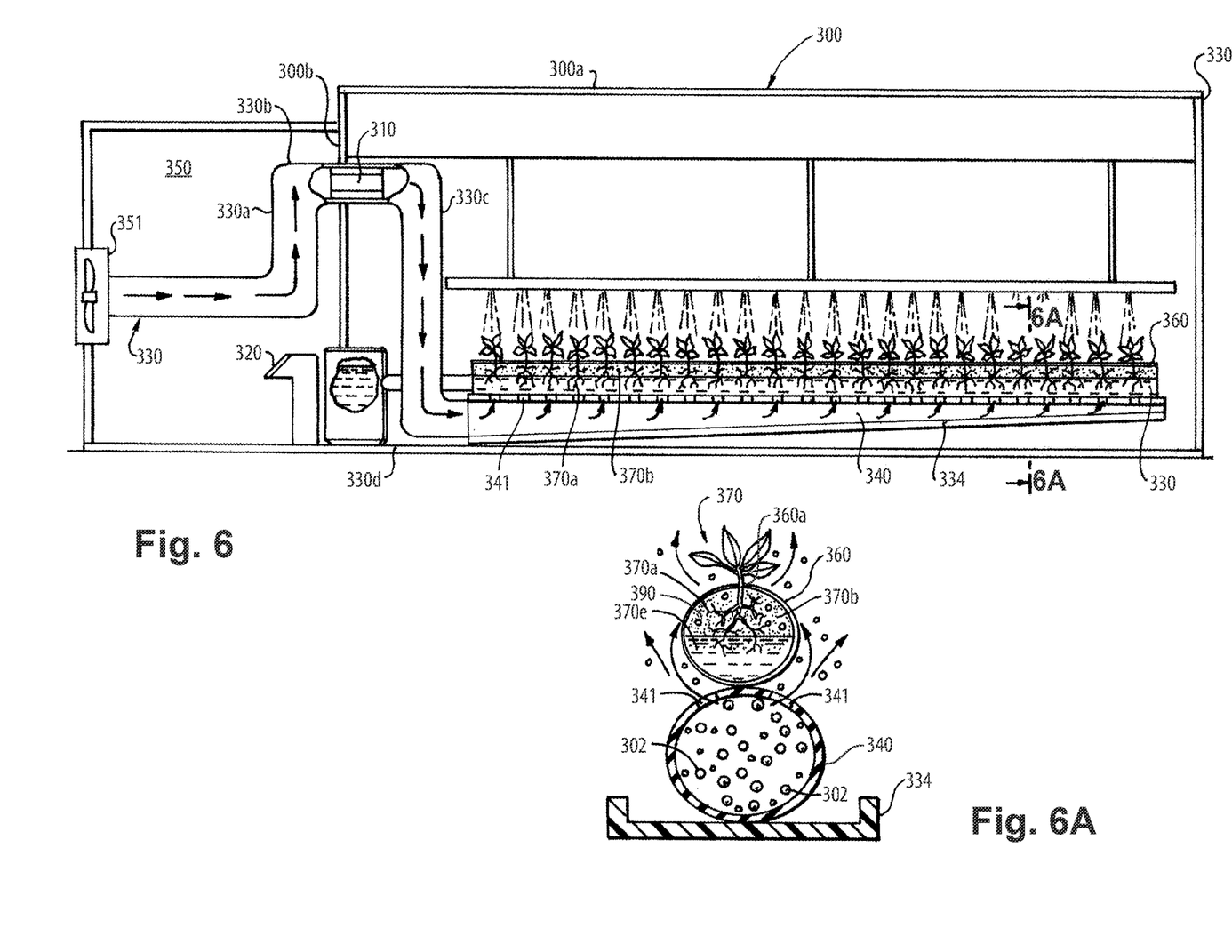
FIG. 6 is a diagrammatic side view and cross section of a greenhouse embodiment, using hydroxyl generators to provide hydroxyl radicals for growing plants.
FIG. 6A is an end view and crossection taken along view lines 6A-6A shown in the greenhouse embodiment of FIG. 6.

In the preferred agricultural hydroponic embodiment, as shown in FIGS. 6 and 6A, the hydroxyl generators can be used in greenhouses, for producing plants hydroponically, such as medicinal or other botanical plants, which are grown agriculturally inside a greenhouse. The plants are mounted in the greenhouse on troughs and tables, typically hydroponically, where the roots are held in place by media, such as coconut fibers, vermiculite, perlite, growstones, rockwool, pine shavings, rice hulls, peat moss, soil, sand or other mineral materials, so that a portion of the roots are soaked in hydroponic fluid, for irrigation and fertigation, and the upper part of the roots are exposed to air, which is brought through with hydroxyl radicals from the hydroxyl generators. For example, in FIG. 6, hydroxyl generator 310 (polygonal-shaped) is positioned in the greenhouse 300 in an air duct 330.

The greenhouse has a top roof area 300a, side walls 300b and 300c, and a base ground level 300d. The greenhouse 300 is adjacent to a utility room 350, which has utility controls 320 for controlling the electronics and mechanics of the system, as well as a hydroponic fluid source 390, which provides the hydroponic fluid through a pipe conduit 360. The pipe 360 has the lower parts of the roots and the media soaking in the fluid, with an upper portion of the roots and media being exposed to air of the plants 370, which have roots 370a held in place by media 370B. The hydroponic fluid 370e is provided through the hydroponic fluid pipe 360. The polygonal-shaped hydroxyl generators 310 are produced in an enclosed air duct, which is preferably a fan 351, and produces an airflow into an air duct 330, which emanates horizontally from the fan 351, or other air source, then makes an upward 90-degree turn, through an air duct portion 330a, which then turns at 90 degrees horizontally at an upper portion of the utility room 350 through a horizontal portion 330b, within which is located the hydroxyl generator, just before a further downward air duct portion 330c emanates downward to the level of trough 334 inside the greenhouse, so that the air from the downward portion 330c of the air duct is then sent horizontally through a flexible sock sleeve 340, having multiple upper apertures 341 to permit the radical hydroxyl flows below and then around the hydroponic fluid pipe, and then contacting the air and plant roots 370a of the plants 370, within the media, such as the coconut fiber 370b. Optionally, an overhead mister hose 365 may be provided in case the plants are not hydroponically bred. In any case, the hydroxyls, whether they are blown or pumped through the root system and media in the greenhouse trough in the hydroponic growing system in the greenhouse, the hydroxyl radicals are exposed to the portions of the roots 370a and growing media 370b, so that they can be misted exposed therein while being irrigated and/or fertigated, either hydroponically, or alternatively within conventional soil media. In this version, the greenhouse 300 is connected to the utility room 350. The hydroxyl generators are installed in a strategic position at the top of the air duct 330b, before the hydroxylated air is sent downward through portion 330c of undulating air duct 330 spanning from utility laboratory room 350 and greenhouse 300 and then the air filled with hydroxyls is sent to the flexible sock sleeve 340, having upper apertures 341 for release of the hydroxyls to intermingle with the plant roots 370a of the hydroponically grown plants 370 located above the parallel troughs 334 of greenhouse 300.

FIG. 6A shows a detailed view of the hydroxyl flexible sleeve 340, with hydroxyls 302 therein and the arrows indicate the flow of the hydroxyls around the lower portion of the pipe with the fertigation and irrigation fluids for the hydroponics where the lower levels of the roots 370a are provided, but where the upper level of the roots exposed to air within the media 370b are then exposed to the hydroxyls of the plants 370. The plants 370 are rooted in the pipe 360, with a stem portion of each plant 370 rising through a crevice 360a in the pipe 360, and a lower portion of the roots 370a being soaked in the hydroponic fluid for irrigation and fertigation, and an upper portion of the roots of 370a being exposed to air flowing out of the sock sleeve 340 into the pipe 360, through the crevice 360a, and in and around the pipe 360. The trough 334 is shown below the flexible sock sleeve 340. The hydroxyls are introduced into air surrounding exposed roots, leaves, stems, vascular or phloem tissues of the plant.

Figure 7:
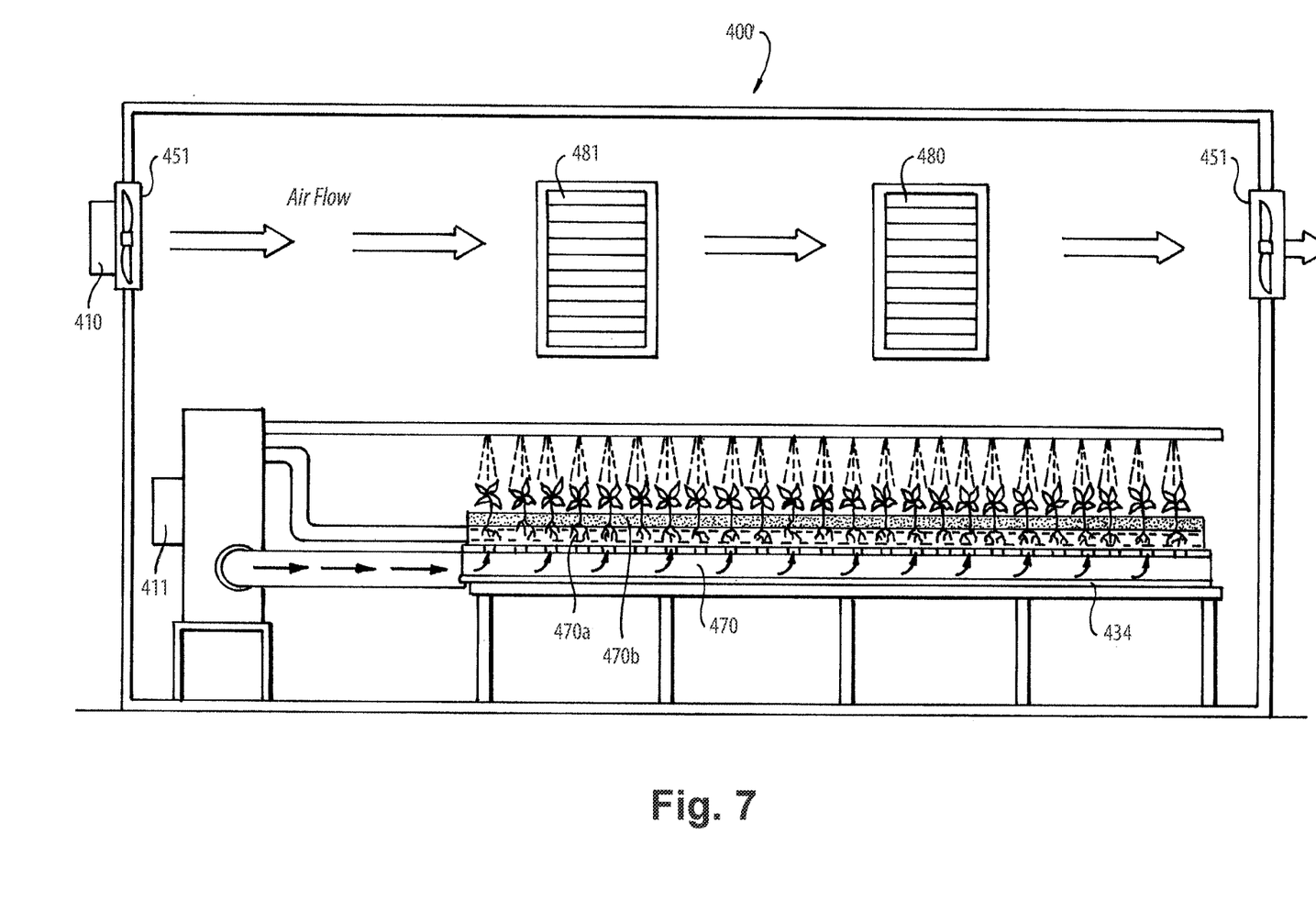
FIG. 7 is a perspective view of an alternate embodiment for a greenhouse for using hydroxyl generators for treating plants.

In an alternate embodiment in a non-hydroponic system, as shown in FIG. 7, a greenhouse 400 includes hydroxyl generators 410 and 411, which are provided either adjacent to an intake fan 451 for airflow through and out the greenhouse 400 through exhaust fan 451 and/or motorized or pressurized shutter outlets 480, 481. A trough 434 is provided for the plants and there may be a drip irrigation hose 470 with apertures for irrigation of hydroponic growing media 470c of the roots 470a of plants 470, where the hydroxyls less generated by hydroxyl generator 411 will mingle within the air exposed portions of the roots and in the media 470b of the plants 470. Optional hydroxyl generator 410 can be located at the intake fan for sending the hydroxyls through the airflow of the greenhouse 400 in areas above the plants.

The hydroxyl generators shown in FIGS. 1-7 will inactivate any VOCs or pathogens, such as virus, bacteria or fungi, anywhere in the air of the buildings FIGS. 1-4, or having the controls of FIGS. 5 and 5A.

In addition, in the greenhouse embodiment, the hydroxyl generators are provided so that the hydroxyl radicals will flow adjacent to and through the media of the plants being farmed therein.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

We claim:

1. An agricultural greenhouse configured to produce plants hydroponically, said agricultural greenhouse comprising:
   a pipe comprising: a plurality of crevices in a top portion of said pipe, at least a portion of said plurality of crevices configured to admit a stem portion of at least one of the plants therethrough;
   plant growing media configured to receive and support roots of plants;
   wherein said plant growing media is received in said pipe;
   a reservoir configured to store hydroponic fluid;
   a conduit in fluid communication with each of said reservoir and a first end of said pipe;
   a control box, said control box configured to control flow of the hydroponic fluid from said reservoir into said pipe to be at a level being part way between a bottom of an interior of said pipe and a top of the interior of said pipe, to continuously soak a bottom portion of the plant roots in said plant growing media in hydroponic fluid, and expose an upper portion of the plant roots within said plant growing media to surrounding air;
   a sock sleeve positioned under said pipe, said sock sleeve comprising: multiple upper apertures;
   wherein a first end of said sock sleeve is open, and a second end of said sock sleeve is closed;
   a trough, said trough being positioned below said sock sleeve, and being configured to support said sock sleeve;
   a hydroxyl generator configured to use UV light to generate hydroxyls;
   an air duct;
   a fan configured to produce a flow of air in said air duct;
   wherein said air duct is configured to deliver the air flow containing hydroxyls generated by said hydroxyl generator to said first end of said sock sleeve;
   wherein the upper portion of the roots of each plant being above the hydroponic fluid are exposed to the air containing hydroxyls flowing out of said sock sleeve, through said multiple upper apertures, and into said plurality of crevices; and
   wherein the air containing hydroxyls flowing out of said sock sleeve through said multiple apertures also thereby causes deactivation of volatile organic compounds, viruses, bacteria, mold, and pathogens present within said agricultural greenhouse.

2. The agricultural greenhouse of claim 1 wherein said trough is positioned and configured to support said sock sleeve at a position whereby said multiple upper apertures in said top of said sock sleeve are positioned directly beneath a bottom outer surface of said pipe.

3. The agricultural greenhouse of claim 1, wherein said control box is further configured to control said fan to thereby control an amount of said air flow, and to control said hydroxyl generator.

4. The agricultural greenhouse of claim 1 wherein said hydroxyl generator is located in an undulating portion of said air duct, being positioned to block the UV light from directly entering into an interior of said agricultural greenhouse.

5. The agricultural greenhouse as in claim 1 wherein said plant growing media is selected from the group consisting of coconut fibers, vermiculite, perlite, growstones, rockwool, pine shavings, rice hulls, peat moss, soil and sand.

6. A method of operating an agricultural greenhouse comprising the steps of:
   forming an air duct;
   creating a flow of air in the duct using a fan;
   positioning a hydroxyl radical generator in the duct;
   emitting ultraviolet light in the duct using a UV lamp in the hydroxyl radical generator;
   generating a stream of hydroxyl radicals within the flow of air in the duct using ultraviolet light (UV) emitted by a UV lamp in the hydroxyl radical generator;
   forming a pipe with a plurality of crevices;
   placing plant growing media in the pipe for supporting growing of stems of plants out of the crevices;
   continuously soaking only a bottom portion of the roots of the plants in the plant growing media in the pipe in hydroponic fluid, and exposing a top portion of the roots growing in the plant growing media to ambient air;
   positioning a hollow sleeve with multiple upper apertures directly below the pipe;
   transmitting the flow of air containing hydroxyl radicals from the duct into the hollow sleeve, causing flowing of the air containing hydroxyl radicals out through the multiple upper apertures and into the plurality of crevices, thereby exposing only the top portion of the roots to a first portion of the hydroxyl radicals, and thereby deactivating impurities including volatile organic compounds (VOCs), viruses, bacteria and mold in the agricultural space by a second portion of the hydroxyl radicals.

7. The method of claim 6 further comprising: regulating a flow of the hydroponic fluid into the pipe using a controller for maintaining a level of the hydroponic fluid part way between a bottom of an interior of the pipe and a top of the interior of the pipe.

8. The method as in claim 6 further comprising: emitting of the ultraviolet light by the UV lamp in the range of between 100 nanometers and 400 nanometers.

9. An agricultural greenhouse comprising:
   a pipe comprising: a plurality of crevices in a top portion of said pipe, at least a portion of said plurality of crevices configured to admit passage of a stem portion of at least one of the plants therethrough;
   plant growing media, wherein said plant growing media is received in said pipe;
   a reservoir configured to store hydroponic fluid, said reservoir being in fluid communication with a first end of said pipe;
   a control box, said control box configured to control flow of the hydroponic fluid from said reservoir into said pipe to be at a level configured to continuously soak a bottom portion of the plant roots in said plant growing media in hydroponic fluid, and expose an upper portion of the plant roots within said plant growing media to surrounding air;
   a sock sleeve positioned under said pipe, said sock sleeve comprising: multiple upper apertures;
   a trough, said trough positioned below said sock sleeve, and configured to support said sock sleeve at a position whereby said multiple upper apertures are positioned directly beneath said pipe;
   a hydroxyl generator configured to use UV light to generate hydroxyls;
   an air duct;
   a fan configured to produce a flow of air in said air duct;
   wherein said air duct is configured to deliver the air flow containing hydroxyls generated by said hydroxyl generator to a first end of said sock sleeve;

wherein the upper portion of the roots of each plant being above the hydroponic fluid are exposed to the air containing hydroxyls flowing out of said sock sleeve, through said multiple upper apertures, and into said plurality of crevices; and wherein the air containing hydroxyls flowing out of said sock sleeve through said multiple upper apertures also thereby causes deactivation of volatile organic compounds, viruses, bacteria, mold, and pathogens present within said agricultural greenhouse.

10. The agricultural greenhouse of claim 9 wherein said hydroxyl generator is located in an undulating portion of said air duct, being positioned to block the UV light from directly entering into an interior of said agricultural greenhouse.

11. The agricultural greenhouse as in claim 9 wherein said plant media is selected from the group consisting of coconut fibers, vermiculite, perlite, growstones, rockwool, pine shavings, rice hulls, peat moss, soil and sand.

12. A method for sanitizing air and surfaces inside of a confined agricultural space comprising the steps of:
    forming an air duct;
    creating a flow of air in the duct using a fan;
    positioning a hydroxyl radical generator in the duct;
    emitting ultraviolet light in the duct using a UV lamp in the hydroxyl radical generator;
    generating a stream of hydroxyl radicals within the flow of air in the duct using the ultraviolet light (UV) emitted by a UV lamp in a hydroxyl generator;
    forming a pipe with a plurality of crevices;
    placing plant growing media in the pipe for supporting growing of stems of plants out of the crevices;
    continuously soaking a bottom portion of the roots of the plants in the plant growing media in the pipe in hydroponic fluid, and exposing a top portion of the roots growing in the plant growing media to ambient air;
    transmitting the flow of air containing hydroxyl radicals from the duct into a hollow sleeve with multiple upper apertures, causing flowing of the air containing hydroxyl radicals out through the multiple upper apertures and into the plurality of crevices, thereby exposing the top portion of the roots to a first portion of the hydroxyl radicals, and thereby deactivating impurities including volatile organic compounds (VOCs), viruses, bacteria and mold in the agricultural space by a second portion of the hydroxyl radicals.

13. The method of claim 12 further comprising:
    positioning the hollow sleeve with multiple upper apertures directly below the pipe; and
    regulating a flow of the hydroponic fluid into the pipe using a controller for maintaining a level of the hydroponic fluid part way between a bottom of an interior of the pipe and a top of the interior of the pipe.

14. The method of claim 12 further comprising: emitting of the ultraviolet light by the UV lamp in the range of between 100 nanometers and 400 nanometers.

15. The method of claim 12 further comprising:
    forming the hollow sleeve using a flexible material; and
    supporting the flexible hollow sleeve using a trough.

16. A hydroxyl radical generator comprising:
    a housing, said housing being elongated and configured to extend from a first end to a second end, and comprising: an air inlet opening at said first end, and an air outlet opening at said second end;
    a first UV lamp;
    a second UV lamp;
    wherein each of said first UV lamp and said second UV lamp are tubular, and each comprises: a bulb formed of medical grade quartz;
    wherein each of said first UV lamp and said second UV lamp are configured to emit/irradiate ultraviolet light in the spectrum of between 100 and 400 nanometers;
    a first lamp mounting flange, said first lamp mounting flange configured to extend across an interior of said housing in proximity to said first end of said housing;
    a second lamp mounting flange, said second lamp mounting flange configured to extend across the interior of said housing in proximity to said second end of said housing;
    a first plurality of spring clasps each fixedly secured to said first lamp mounting flange;
    a second plurality of spring clasps each fixedly secured to said second lamp mounting flange;
    wherein said first plurality of spring clasps are configured to mount distal ends of each of said first and second UV lamps proximate to said first end of said housing, and wherein said second plurality of spring clasps are configured to mount distal ends of each of said first and second UV lamps proximate to said second end of said housing, and wherein said first and second UV lamps thereby extend substantially parallel to a lengthwise direction of said housing; and
    wherein each of said first and second UV lamps have a length configured to extend substantially an entire length from said first end of said housing to said second end of said housing to thereby expose ambient water vapor within air passing through said housing from said first end to said second end to the ultraviolet light to create hydroxyl radicals, for use in deactivating volatile organic compounds, viruses, bacteria, mold, and pathogens.

17. The hydroxyl radical generator according to claim 16,
    wherein said housing comprises: an octagonal cross-sectional shape;
    wherein said first and second UV lamps are symmetrically mounted and centrally positioned within said octagonal cross-sectional shape of said housing; and
    wherein interior surfaces of said housing comprise: a reflective coating configured to cause the hydroxyl radicals created therein to bounce off said reflective coating and decontaminate the air and at least the interior surfaces within said housing.

18. The hydroxyl radical generator according to claim 16, further comprising:
    a sensor;
    wherein said control box is configured to sequence operation of said first UV lamp and said second UV lamp;
    wherein said control box is configured to activate said first UV lamp when said hydroxyl radical generator is turned on; and
    wherein said control box is configured to additionally activate said second UV lamp when said sensor detects an abnormal intrusion of VOCs' or pathogens.

19. The hydroxyl radical generator according to claim 18, wherein said control box is configured to communicate wirelessly with each of said first UV lamp and said second UV lamp to control said sequenced operation of said first UV lamp and said second UV lamp.

20. The hydroxyl radical generator according to claim 19, further comprising:
an airflow sensor; and
wherein said control box is configured to shut down said first UV lamp and said second UV lamp when air flow is not detected by said airflow sensor.

21. The hydroxyl radical generator according to claim 20,
wherein said housing is formed of a first clamshell housing portion and a second clamshell housing portion;
wherein said first clamshell housing portion is hinged with respect to said second clamshell housing portion, thereby permitting replacement of said first and second UV lamps.

22. The hydroxyl radical generator according to claim 21, further comprising:
a proximity switch; and
wherein said control box is configured to shut down said first UV lamp and said second UV lamp when said proximity switch detects an opening between said first clamshell housing portion and said second clamshell housing portion.

23. The hydroxyl radical generator according to claim 22, further comprising:
a light sensor configured to detect light emitted by each of said first and second UV lamps;
wherein said light sensor is configured to provide feedback to indicate when to replace said first UV lamp and said second UV lamp.

* * * * *